United States Patent
Aime et al.

(10) Patent No.: US 8,784,778 B2
(45) Date of Patent: Jul. 22, 2014

(54) MRI CONTRAST AGENTS ENDOWED WITH CONCENTRATION INDEPENDENT RESPONSIVENESS

(75) Inventors: Silvio Aime, Carignano (IT); Enzo Terreno, Bidiana (IT)

(73) Assignee: Bracco Imaging S.p.A., Milan (IT)

( * ) Notice: Subject to any disclaimer, the term of this patent is extended or adjusted under 35 U.S.C. 154(b) by 1295 days.

(21) Appl. No.: 11/919,529

(22) PCT Filed: Apr. 28, 2006

(86) PCT No.: PCT/EP2006/004023

§ 371 (c)(1),
(2), (4) Date: Oct. 29, 2007

(87) PCT Pub. No.: WO2006/117166

PCT Pub. Date: Nov. 9, 2006

(65) Prior Publication Data

US 2009/0022668 A1    Jan. 22, 2009

(30) Foreign Application Priority Data

Apr. 29, 2005 (EP) .................................... 05103567

(51) Int. Cl.
*A61K 49/18* (2006.01)
*A61K 49/10* (2006.01)

(52) U.S. Cl.
USPC ..... 424/9.321; 424/1.11; 424/1.41; 424/9.32; 424/9.36

(58) Field of Classification Search
USPC ............. 424/1.11, 1.41, 1.49, 9.3, 9.35, 9.32, 424/9.321, 9.6; 540/937
See application file for complete search history.

(56) References Cited

U.S. PATENT DOCUMENTS

| | | | |
|---|---|---|---|
| 5,780,010 A * | 7/1998 | Lanza et al. | 424/9.32 |
| 5,965,131 A * | 10/1999 | Griffiths et al. | 424/133.1 |
| 6,673,333 B1 * | 1/2004 | Meade et al. | 424/9.35 |
| 2002/0009416 A1 | 1/2002 | Schechter et al. | |
| 2008/0145311 A1 * | 6/2008 | Lanza et al. | 424/1.21 |

FOREIGN PATENT DOCUMENTS

| | | |
|---|---|---|
| EP | 1106186 A2 | 6/2001 |
| EP | 1302465 A1 | 4/2003 |
| EP | 1106186 A3 | 8/2003 |
| EP | 1466629 A1 | 10/2004 |

OTHER PUBLICATIONS

A. Dean Sherry et al. Angew. Chem. Int. Ed., 1999, 38(21) 3192-3194.*

Silvia Morel et al. NMR relaxometric investigations of solid lipid nanoparticles (SLN) containing gadolimium (III) complexes, European Jounal of Pharmaceutics and Biopharmaceutics, 45, 157-163, 1998.*

Yan Guoping et al. Research Progress of magnetic resonance imaging contrast agents, Cihnese Science Bulletin vol. 46(15), 1233-1237, 2001.*

PCT Search Report for PCT/EP2006/004023, mail date Jan. 15, 2007.

PCT Written Opinion of the ISA for PCT/EP2006/004023, mail date Jan. 15, 2007.

Aime, S. et al: "High-resolution NMR and relaxometric studies of Ln(III) complexes of Relevance to MRI", Journal of Alloys and Compounds, Elsevier Sequoia, Lausanne, CH, vo. 225, Jul. 15, 1995 pp. 274-278, XP004072071, ISSN: 0925-8388.

Aime, S. et al: "Non-covalent Conjugates Between Cationic Polyamino Acids and GDIII Chelates: A Route for Seeking Accumulation of MRI-Contrast Agents at Tumor Targeting Sites" Chemistry—A European Journal, VCH Publishers, US, vol. 6, No. 14, Jul. 14, 2000, pp. 2609-2617, XP001113062, ISSN: 0947-6539.

Led, J.J. et al: "Paramagnetic Carbon-13 NMR Relaxation Studies on the Kinetics and Mechanism of the Biocarbonate-Carbon Dioxide Exchange Catalyzed by Manganest-II Human Carbonic Anhydrase I", Biochemistry, vol. 26, No. 1, 1987, pp. 183-192, XP002372517, ISSN: 0006-2960.

Lebudskova, P. et al: "A Gadolinium (III) Complex of a Carboxylic-Posphorus Acid Derivative of Diethylenetriamine Covalently Bound to Inulin, a Potential Macromolecular MRI Contrast Agent" Bioconjugate Chemistry, ACS, Washington, DC, US, vol. 15, No. 4, Jul. 2004 pp. 881-889, XP001236870, ISSN: 1043-1082.

Zhang, S. et al: "A Novel PH-sensitive MRI Contrast Agent", Angewandte Chemie. International Edition, Wiley VCH Verlag, Weinheim, DE, vol. 38, No. 21, Nov. 2, 1999 pp. 3192-3194, XP000864995, ISSN: 1433-7851.

* cited by examiner

*Primary Examiner* — Michael G Hartley
*Assistant Examiner* — Jagadishwar Samala
(74) *Attorney, Agent, or Firm* — M. Caragh Noone (57) ABSTRACT

The present invention relates to a method for the in vivo, ex vivo, or in vitro determination of physical or chemical parameters of diagnostic interest by use of a slow tumbling paramagnetic agent that is responsive to changes of said physical or chemical parameter through changes in the $R_{2p}/R_{1p}$ ratio allowing the determination of the said parameter in a manner that is independent on the actual agent concentration.

9 Claims, 12 Drawing Sheets

MRI CONTRAST AGENTS ENDOWED WITH CONCENTRATION INDEPENDENT RESPONSIVENESS

This application is the national stage application of corresponding international application number PCT/EP2006/004023 filed Apr. 28, 2006, which claims priority to and the benefit of the European application no. 05103567.3, filed Apr. 29, 2005, all of which are hereby incorporated by reference.

The present invention relates to the field of diagnostic imaging by use of Magnetic Resonance Imaging techniques (MRI). More in particular, it relates to a new use of a class of paramagnetic contrast agents in a method for the in vivo determination of physical or chemical parameters of diagnostic interest, independently from the local concentration of the administered contrast agent.

BACKGROUND OF THE INVENTION

It is now well established that the potential of Magnetic Resonance Imaging (MRI) procedures can be further enhanced when this diagnostic modality is applied in conjunction with the administration of contrast agents (CAs), i.e. chemicals able to promote marked changes in the relaxation rates of the tissue protons. The MRI CAs are principally represented by paramagnetic complexes, mostly containing Gd(III), Fe(III) or Mn(II) ions, which affect the relaxation rates of the bulk water through the exchange of the water molecules in their coordination spheres (Caravan P, et al. Chem Rev 1999, 99:2293-2352; the Chemistry of Contrast Agents in Medical Magnetic Resonance Imaging. Chichester, UK: John Wiley & Sons; 2001. p 45-120).

The efficacy of a paramagnetic complex is assessed by its proton relaxation enhancement or relaxivity ($r_i$, i=1, 2), which represents the increase of the proton relaxation rate of an aqueous solution containing 1 mM concentration of the paramagnetic agent in comparison to the proton relaxation rate of neat water. For a paramagnetic complex, the proton relaxation enhancement is chiefly governed by the choice of the paramagnetic metal, the rotational correlation time of the complex and the accessibility of the metal to the surrounding water molecules, i.e. the rapid exchange of water with the bulk.

Two characteristic relaxation rates are involved: $R_1$ that is defined as the inverse of the longitudinal relaxation time or spin lattice relaxation time $T_1$, i.e. $1/T_1$, and $R_2$ that is defined as the inverse of the transverse relaxation time or spin-spin relaxation time $T_2$, i.e. $1/T_2$.

The higher the longitudinal relaxivity ($r_1$), the larger is the signal enhancement detected in the corresponding $T_1$-weighted MR images and the better is the contrast differentiation in the resulting images.

Some contrast agents exist which relaxivity is related to and may depend upon the physical or chemical characteristics of the microenvironment in which they distribute. These agents are known as responsive agents because the contrast, in the image they promote, is responsive to a physical or chemical parameter of diagnostic interest. Several systems have been reported which relaxivity is made dependent on pH, temperature, $PO_2$, enzymatic activity, ion and metabolite concentrations (Jacques V, Top Curr Chem 2002, 221, 123-164).

However, such a peculiar responsive property could not have been properly exploited in practice because the detected $T_1$-variations cannot be unambiguously ascribed to a change in relaxivity and, consequently, to a variation on the physical or chemical parameter under examination, if the actual concentration of the paramagnetic complex is unknown. To be effective, a MRI responsive agent should display its responsiveness in a concentration independent mode. Accordingly, it is an object of the present invention a MRI method and agents allowing the overcoming of this drawback.

SUMMARY OF THE INVENTION

In accordance with the above object, the present invention is directed to the identification of a class of responsive agents which use allows the measurement of a physical or chemical parameter of diagnostic interest independently on the actual concentration of the agent itself. In a different aspect, the invention relates to a method of use of said agents for the determination of a physical or chemical parameter of diagnostic interest, independently on the absolute concentration of the administered agent.

BRIEF DESCRIPTION OF THE FIGURES

FIG. 4 shows the temperature dependence of the $R_{2p}/R_{1p}$ ratio for the (Gd-1)$_4$/Avidin adduct at 7 T. The formula of the Gd-1 complex is included in the experimental section. The reported bars refer to the standard deviation of three measurements of solutions containing 0.125, 0.25, and 0.5 mM of the paramagnetic complex.

DESCRIPTION OF THE INVENTION

A class of contrast agents that solve the problem faced by the present invention is represented by responsive paramagnetic systems that are responsive to a physical or chemical parameter of diagnostic interest in terms of affecting $T_1$ and $T_2$ of the solvent water protons, and in which such $T_1$ and $T_2$ responsiveness to said parameter follows different behavioral functions. For these responsive systems the $R_{2p}/R_{1p}$ ratio may be made independent upon the actual concentration of the agent itself through maintaining the functional dependence thereof to the parameter of interest. Accordingly, by use of these systems, a determination of the parameter of interest may be obtained as independent on the actual agent concentration through the measurement of such $R_{2p}/R_{1p}$ ratio.

In the present invention, unless otherwise indicated, with physical or chemical parameter of diagnostic interest we intend a parameter selected from: temperature, pH, partial pressure of oxygen ($PO_2$) or carbon dioxide ($PCO_2$), specific ion or metabolite concentration, or specific enzymatic activity.

By knowing the value of the said physical or chemical parameter(s), a skilled man in the art may easily provide diagnostic evaluations of any physiological or metabolic process of diagnostic interest relying on the said parameter(s).

For protons dipolarly coupled to a paramagnetic center, at magnetic field strengths higher than 0.2 T, the $R_{2p}$ and $R_{1p}$ terms (wherein $R_{2p}$ is the paramagnetic contribution to the measured transverse relaxation rate and $R_{1p}$ is the paramagnetic contribution to the measured longitudinal relaxation rate) in the presence of a macromolecular Gd(III) complex are described by the following equations:

$$R_{1p} = \frac{P_M}{T_{1M} + \tau_M} \Rightarrow \frac{1}{T_{1M}} = \frac{6}{15} \frac{K^{DIP}}{r_H^6}\left(\frac{\tau_C}{1 + \omega_H^2 \tau_C^2}\right) \quad (1)$$

$$R_{2p} = \frac{P_M}{T_{2M} + \tau_M} \Rightarrow \frac{1}{T_{2M}} = \frac{1}{15} \frac{K^{DIP}}{r_H^6}\left(4\tau_C + \frac{3\tau_C}{1 + \omega_H^2 \tau_C^2}\right) \quad (2)$$

where $P_M$ is the molar fraction of the mobile protons dipolarly interacting with Gd(III) ion (e.g. for one water molecule in the inner coordination sphere of Gd(III), $P_M$ is equal to $$\frac{q[GdL]}{55.6}$$

with q=number of water molecule coordinated to Gd(III)), $\tau_M$ is their mean residence lifetime, $r_H$ their mean distance from the metal center, $\omega_H$ their Larmor frequency (rad·s$^{-1}$), and $\tau_C$ their molecular correlation time ($\tau_C^{-1} = \tau_M^{-1} + \tau_R^{-1} + \tau_{1S}^{-1}$ with $\tau_R$=rotational correlation time or reorientational time and $\tau_{1S}$=longitudinal electronic relaxation time). $K^{DIP}$ is a constant value (3.887·10$^{-42}$ m$^6$·s$^{-2}$) related to the dipolar interaction between the electron and the nuclear spins.

From equations 1-2 it may be derived that for said macromolecular agent the $R_{2p}/R_{1p}$ ratio is independent on the concentration of the agent itself, being only affected by $\tau_M$, $\tau_R$, $\tau_{1S}$ and $\omega_H$ values. Accordingly, for these compounds, changes in the $R_{2p}/R_{1p}$ ratio acting as a reporter of a change in the parameter of interest are only related to a change in $\tau_R$ and/or $\tau_M$ and/or $\tau_{1S}$ where such changes have a different effect on $R_{2p}$ and $R_{1p}$ values.

Therefore, a first object of the present invention is the use of a slow tumbling paramagnetic agent responsive to changes of a given physical or chemical parameter of diagnostic interest through changes in $R_{2p}/R_{1p}$ ratio for the preparation of diagnostic compositions for the determination of the said parameter in a human or animal body organ, fluid or tissue, by use of the MRI, in a manner which is independent on the absolute concentration of said administered agent.

A further object of the present invention is a method for the in vivo, or in vitro or ex vivo determination, by use of MRI, of a physical or chemical parameter of diagnostic interest in a human or animal body organ, fluid or tissue, which method comprising:

administering to said human or animal a diagnostically effective amount of a slow tumbling paramagnetic agent that is responsive to microenvironmental changes of said parameter through changes in the $R_{2p}/R_{1p}$ ratio, and recording a MRI imaging responsive for said parameter, that is independent on the actual concentration of the administered agent, through the measurement of said ratio.

The term "diagnostically effective amount" as used herein, refers to any amount of the slow tumbling paramagnetic agent of the invention, or pharmaceutical composition thereof, that is sufficient to fulfil its intended diagnostic purpose(s), i.e. to provide highly contrasted and diagnostically effective images enabling the determination of the parameter of interest.

The said dosages are obviously selected by the health professional depending on the administered slowly mowing agent.

According to the present invention with "slow tumbling paramagnetic agent or system" as used herein interchangeably, we intend a paramagnetic agent or system having a $\tau_R$ value ≤1 ns.

In one preferred aspect of the invention the said slow tumbling paramagnetic agent is a macromolecular paramagnetic metal complex.

In another aspect, the said slow tumbling paramagnetic system is represented by a paramagnetic system in which the relaxation enhancement is generated by magnetic susceptibility effects.

Such effects, which are strictly limited to the transverse evolution of the nuclear magnetization (i.e. they only affect $T_2$ values), are induced by microscopic magnetic field gradients created by magnetic susceptibility differences between compartments (J L Boxerman, R M Weisskoff, B R Rosen "Susceptibility effects in Whole Body Experiments" in "Methods in Biomedical Magnetic Resonance Imaging and Spectroscopy" Ed. I R Young, John Wiley & Sons, Chichester, Vol. 1, pp 654, 2000).

This $T_2$-specific contribution is directly dependent on the square of the intensity of the magnetic field gradients that are proportional to the magnetic susceptibility differences and the magnetic field strength, and they are affected by the relative size of the compartments. The difference of the magnetic susceptibility between the compartments can be significantly enhanced if a rather high concentration of a paramagnetic species is confined in one compartment. Typical examples of slow tumbling paramagnetic systems generating a significant susceptibility $T_2$-effect are represented by nano-sized compartments containing rather high amount of a paramagnetic metal complex.

According to the present invention, unless otherwise indicated, with the term "nano-sized systems" we intend a system having a mean diameter ≥5 nm. Preferably, the said systems entrap the paramagnetic metal complex at a minimum concentration of 5 mM.

A non-exhaustive list of nano-sized systems that can entrap paramagnetic metal complexes includes, for instance, nanoparticles, microemulsions, liposomes, protein cavities, and the like.

In other words, as for all the macromolecular paramagnetic metal complexes according to the invention, for the said nano-sized systems the $R_{2p}/R_{1p}$ ratio is independent on the concentration, being it only affected by the magnetic field strength, the amount of the entrapped complex and the size of the compartment. In an embodiment of the invention, accordingly, the slow tumbling paramagnetic agent displaying a $R_{2p}/R_{1p}$ ratio responsive to microenvironmental changes of a physical or chemical parameter of diagnostic interest is represented by a nano-sized system which transverse relaxation rate is affected by magnetic susceptibility effects for which, moreover, the $R_{2p}$ value, and consequently the $R_{2p}/R_{1p}$ ratio, is dependent on a physical or chemical parameter or a physiological or metabolic process of diagnostic interest.

Besides the selective $T_2$-effect arising from magnetic susceptibility effects, the $R_{2p}/R_{1p}$ ratio for a nano-sized system could be made dependent on the parameter of interest by acting on $R_{1p}$. For instance, this goal may be achieved if the physico-chemical parameter affects the water permeability of the compartment that entraps the paramagnetic complex.

Thus, in one embodiment, the present invention relates to a method for the in vivo, or in vitro or ex vivo determination, by use of MRI, of a physical or chemical parameter of diagnostic interest in a human or animal body organ, fluid or tissue in which a nano-sized system entrapping a paramagnetic metal complex is administered that is responsive to changes of a given physical or chemical parameter or a physiologic or metabolic process of diagnostic interest through changes in $R_{2p}/R_{1p}$ ratio.

As above said, for the particular class of slow tumbling paramagnetic agent of the invention, the $R_{2p}/R_{1p}$ ratio is independent on the actual concentration of the agent itself, while the said ratio is only affected by $\tau_M$, $\tau_R$, $\tau_{1S}$, size, water permeability of the compartment, and $\omega_H$ values.

So, from a different point of view, it may be said that the measured $R_{2p}/R_{1p}$ ratio for the said agents acts as a reporter of a change in the parameter of interest because the changes that the said parameter promote in $\tau_R$ and/or $\tau_M$ and/or $\tau_{1S}$ values, and/or size, and/or water permeability of the compartment, at a given $\omega_H$ value, have a different effect on $R_{2p}$ and $R_{1p}$ values.

In particular, when the slow tumbling paramagnetic system used in the method of the invention is a macromolecular paramagnetic metal complex, the measured $R_{2p}/R_{1p}$ ratio acts as a reporter of a change in the parameter of interest because the changes that the said parameter promotes in $\tau_R$ and/or $\tau_M$ and/or $\tau_{1S}$ values, at a given $\omega_H$ value, have a different effect on $R_{2p}$ and $R_{1p}$ values.

When, in a different embodiment, the administered slow tumbling paramagnetic system is a nano-sized system entrapping a paramagnetic metal complex, the measured $R_{2p}/R_{1p}$ ratio acts as a reporter of a change in the parameter of interest because the changes that the said parameter promotes in the size, and/or water permeability of the compartment have a different effect on $R_{2p}$ and $R_{1p}$ values. The ratiometric method for responsive agents as per the present invention relies, accordingly, on the exploitation of the differential effect that the correlation times $\tau_R$, $\tau_M$ and $\tau_{1S}$ have on $R_{1p}$ and $R_{2p}$ values for slowly tumbling paramagnetic metal complexes.

In a different aspect, the said ratiometric method may further relies on the exploitation of the specific effect on $R_{2p}$ values caused by the presence of magnetic susceptibility effects when the slow tumbling paramagnetic systems is a nano-sized systems entrapping a paramagnetic complex.

Figure 1:
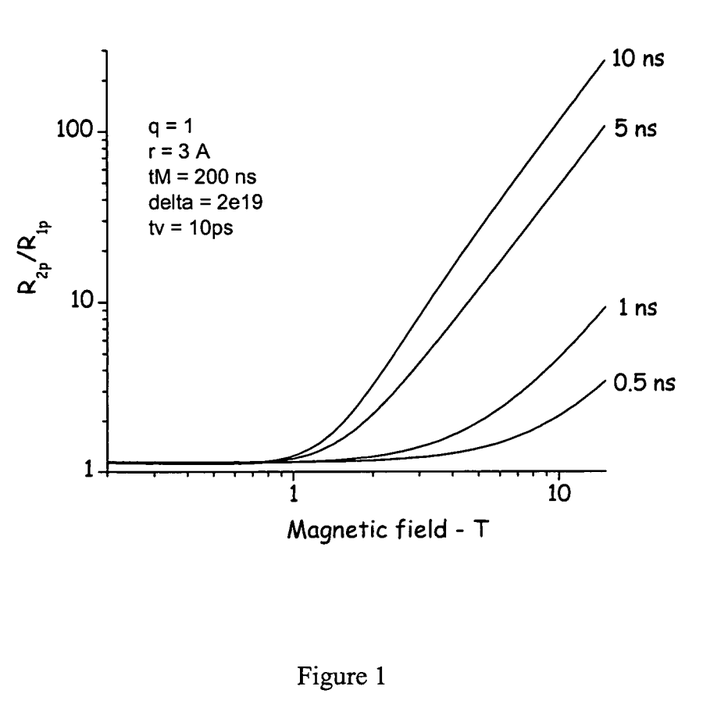
FIG. 1 relates to calculated $R_{2p}/R_{1p}$ values as a function of the magnetic field strength for a macromolecular Gd(III) complex (q=1, r=3 Å, $\tau_M$=200 ns) endowed with $\tau_R$ values in the 0.5-10 ns range. For the electronic relaxation, a $\Delta^2$ value of $2 \cdot 10^{19}$ s$^{-2}$ and a $\tau_V$ value of 10 ps (corresponding to $\tau_{1S}$ values in the 0.65-500 ns interval) have been used.

With the aim to define how to suitably select such $\tau_M$, $\tau_R$, $\tau_{1S}$ and $\omega_H$ values and, consequently, how to define the macromolecular paramagnetic metal complex that may advantageously be used in the method of the invention, a first theoretical simulation based on Eqs. 1-2 has been performed showing that, at the magnetic field strengths used in MRI (0.2-7 T), the $R_{2p}/R_{1p}$ ratio begins to be sensitive to the rotational mobility of the Gd(III) complex ($\tau_R$) for $\tau_R$ values longer than 0.5 ns, wherein $\tau_R$ values longer than 1 ns are preferred and values longer than 5 ns are even more preferred (FIG. 1).

Figure 2A:
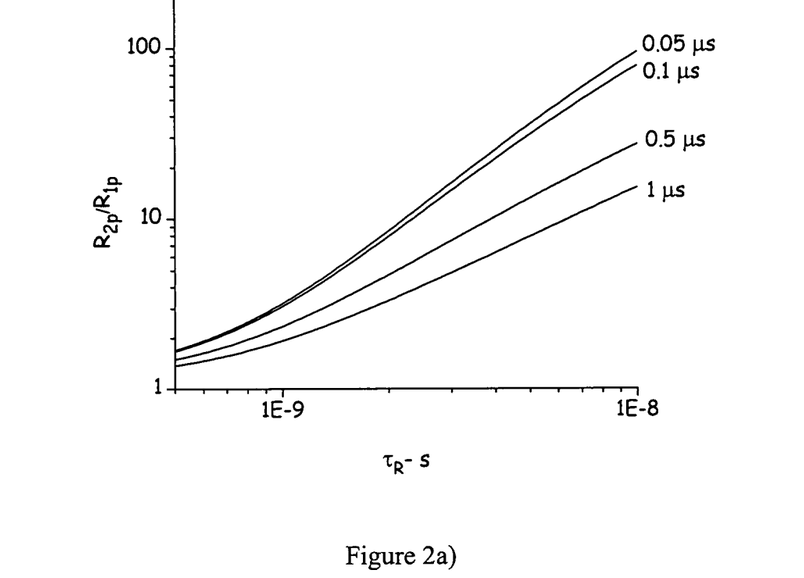
FIG. 2a) relates to calculated $R_{2p}/R_{1p}$ values as a function of $\tau_R$ for Gd(III)-based systems endowed with $\tau_M$ values in the 0.05-1 µs range at 7 T.
Figure 2B:
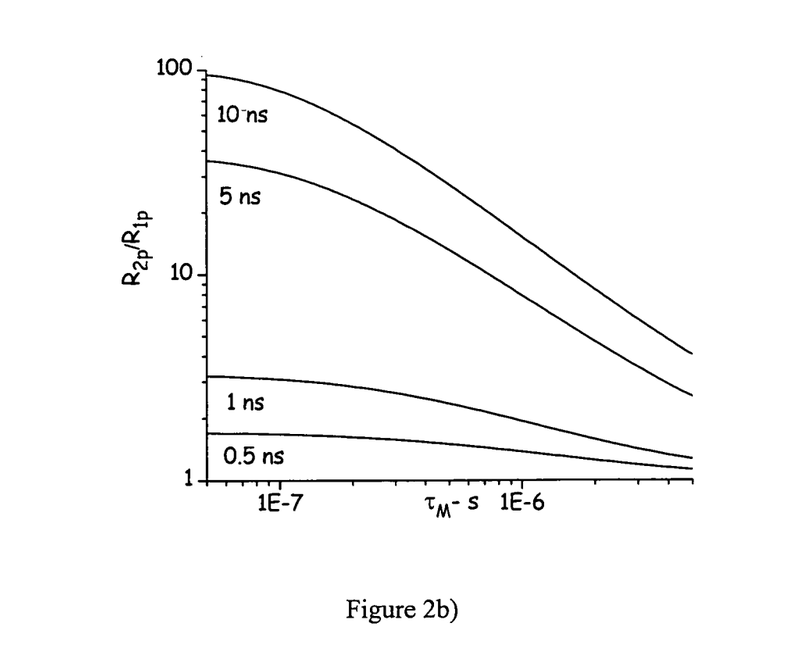
FIG. 2b) relates to calculated $R_{2p}/R_{1p}$ values as a function of $\tau_M$ for Gd(III)-based systems endowed with $\tau_R$ values in the 0.5-10 ns range at 7 T.

Once the magnetic field strength is settled, $\tau_R$ and $\tau_M$ values have an opposite effect on the $R_{2p}/R_{1p}$ ratio as it may be derived by looking at the additional simulations performed and reported in FIG. 2 a) and b). In the simulation of FIG. 2a) the $R_{2p}/R_{1p}$ values have been reported as a function of $\tau_R$ for Gd(III)-based systems endowed with $\tau_M$ values in the 0.05-1 μs range at 7 T. In the simulation of FIG. 2b) $R_{2p}/R_{1p}$ values have been calculated as a function of $\tau_M$ for Gd(III)-based systems endowed with $\tau_R$ values in the 0.5-10 ns range at 7 T. From equations 1 and 2 it follows that $\tau_R$ affects the $R_{2p}/R_{1p}$ ratio through its effect on $\tau_C$ and consequently on $T_{iM}$ (i=1,2), whereas $\tau_M$ influences $R_{2p}/R_{1p}$ through the limiting effect on Rip via the $(T_{iM}+\tau_M)$ term.

Based on these results, a preferred class of responsive agents for use in the method of the invention may comprise macromolecular paramagnetic complex compounds endowed with both dipolarly coupled protons and $\tau_R$ value ≥1 ns, provided that their rotational mobility ($\tau_R$) and/or the mean residence lifetime $\tau_M$ of the mobile protons dipolarly coupled to their metal center and/or their longitudinal electronic relaxation time $\tau_{1S}$ are dependent on the parameter of interest. For a given compound, it is well known in the art that the dependence of the said $\tau_R$, $\tau_M$, $\tau_{1S}$ values on the parameter of interest may be easily verified by plotting of the $R_{2p}/R_{1p}$ ratio over the said parameter: when a significant variation of the said ratio over the parameter of interest is verified, then $\tau_R$ and/or $\tau_M$ and/or $\tau_{1S}$ of the tested compound are dependent on this parameter.

Among the said responsive agents, particularly preferred are macromolecular paramagnetic metal complex compounds endowed with $\tau_R$ values from 1 to 10 ns and $\tau_M$ values from 0.01 to 1 μs.

In the present description, unless otherwise indicated, with the term macromolecular paramagnetic complex it has to be intended a paramagnetic metal complex endowed with slow tumbling rate, that is to say a complex endowed with a $\tau_R$ value longer than 0.5 ns, wherein $\tau_R$ values longer than 1 ns are preferred and values from 5 to 10 ns are even more preferred.

The necessary slow tumbling rate of the responsive agents according to the invention may be obtained by controlling the molecular size of the paramagnetic system, for example trough the formation of covalent or non-covalent linkages with macromolecules or endogenous substrates that confer to the agent the desired molecular weight.

For nano-sized responsive agents of the invention, for example, the preferred systems are nanoparticles with a mean diameter ≥5 nm, entrapping a paramagnetic metal complex at a minimum concentration of 5 mM.

The paramagnetic complex entrapped in the said nano-sized system may be any paramagnetic metal complex of the art, without any limitation concerning its molecular weight.

As far as temperature responsive nano-sized agents is concerned, a preferred system (for imaging experiments performed at magnetic fields ≥3 T) may be represented by a paramagnetic liposome endowed with the following characteristics: i) mean diameter ≥150 nm, ii) water permeability of the liposome membrane ≥5·10$^{-5}$ cm s$^{-1}$, iii) concentration of the entrapped paramagnetic metal complex (referred to the inner aqueous compartment of the liposome) ≥50 mM. Preferably, the entrapped paramagnetic metal complex is a Gd(III) complex.

In the present description, with the term paramagnetic contrast agent or paramagnetic complex or paramagnetic metal complex, as used herein interchangeably, we intend any chelated complex with a bi- and trivalent paramagnetic metal ion, preferably having atomic number ranging between 20 and 31, 39, 42, 43, 44, 49, and between 57 and 83 such as, for instance, $Fe^{2+}$, $Fe^{3+}$, $Cu^{2+}$, $Cr^{3+}$, $Eu^{3+}$, $Dy^{3+}$, $La^{3+}$, $Yb^{3+}$ or $Mn^{2+}$ and $Gd^{3+}$, this latter being even more preferred.

More preferably, the slow tumbling responsive agent for use in the method of the invention is a macromolecular Gd(III) complex endowed with a $\tau_R$ value between 1 and 10 ns, a $\tau_M$ from 0.01 to 1 µs for which, moreover, $\tau_R$ and/or $\tau_M$ and/or $\tau_{1S}$ are dependent on the parameter of interest.

Accordingly, in a preferred method according to the invention, a slowly moving Gd(III) complex is used having a $\tau_R$ value from 1 to 10 ns and a $\tau_M$ from 0.01 to 1 µs and wherein $\tau_R$ and/or $\tau_M$ and/or $\tau_{1S}$ are dependent on the parameter of interest.

In a equally preferred method of the invention, a slowly moving nano-sized agent is used having a mean diameter ≥5 nm and entrapping a paramagnetic complex with a concentration equal or greater than 5 mM for which the size of the system and/or the magnetic susceptibility effects are dependent on a parameter of diagnostic interest.

For general, non-exhaustive, reference to the paramagnetic metal complexes or to the nano-sized systems entrapping a paramagnetic metal complex as per the invention, see, for instance, the experimental section below.

The paramagnetic complexes of the invention can also conveniently be in the form of physiologically acceptable salts. Preferred cations of inorganic bases that can be suitably used to salify the complexes of the invention comprise ions of alkali or alkaline-earth metals such as potassium, sodium, calcium or magnesium.

Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids that can be suitably used to salify the complexes of the invention comprise the ions of halo acids such as chlorides, bromides, iodides or other ions such as sulfate.

Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine, ornithine or of aspartic and glutamic acids. A further object of the present invention is a diagnostic composition for use in the MR Imaging of a physical or chemical parameter of diagnostic interest comprising at least one slowly moving paramagnetic complex or system endowed with a $\tau_R$ value from 1 to 10 ns and $\tau_M$ value from 0.01 to 1 µs for which, moreover, the rotational mobility $\tau_R$ and/or the mean residence lifetime $\tau_M$ of the mobile protons dipolarly coupled to the metal center and/or the longitudinal electronic relaxation time $\tau_{1S}$ are dependent on the said parameter of interest.

In one embodiment of the invention, the said diagnostic composition comprises a nano-sized system entrapping a 5 mM solution of a paramagnetic complex, that is responsive to microenvironmental changes of a given physical or chemical parameter or a physiologic or metabolic process of diagnostic interest through changes in the $R_{2p}/R_{1p}$ ratio and for which the size of the system and/or the magnetic susceptibility effects are dependent on a parameter of diagnostic interest.

EXPERIMENTAL SECTION

A non-limiting list of preferred slow tumbling systems of the invention is reported in the following section, to better exemplify the wide applicative potential of the present invention.

Example 1

As a proof of principle, the responsive properties of a macromolecular Gd(III) complex towards temperature, a parameter whose non-invasive measurement in vivo is important either for diagnostic or for therapeutic purposes, have been investigated.

Figure 3:
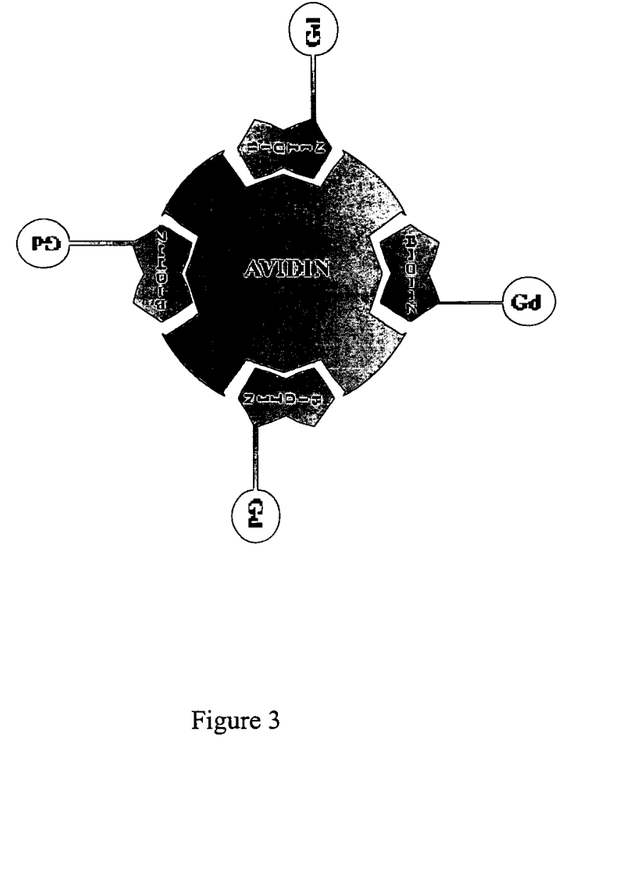
FIG. 3 shows the structure of the (Gd-1)$_4$/Avidin adduct.

Among a number of possibilities, the adduct formed by four units of complex 1 and Avidin was chosen as slowly moving system. Complex 1 is a derivative of GdDTPA bearing on its surface a biotin moiety. The structure of this complex is reported below. GdDTPA is the most representative example of MRI contrast agents, already marketed with the name Magnevist®. Avidin is a tetrameric glycoprotein (MW of ca. 68 kDa) which strongly binds ($K_A=10^{15}$) (Green N M, Adv Prot Chem 1975, 29, 85 133) four biotin units (FIG. 3).

Gd-1

The $R_{2p}/R_{1p}$ protocol for the temperature measurement was tested on three solutions containing different amounts of (Gd-1)$_4$/Avidin adduct (in PBS buffer at pH 7.4). The concentration of Gd-1 in the three solutions was 0.125, 0.25, and 0.5 mM, respectively. $R_1$ and $R_2$ values for water protons were measured at 7.05 T (corresponding to a proton Larmor frequency of 300 MHz) for each solution in the temperature range 298-318 K.

The paramagnetic $R_{1p}$ and $R_{2p}$ contributions to the observed relaxation rates were obtained by subtracting the corresponding diamagnetic contributions ($R_{id}$) measured for each temperature in the absence of the paramagnetic agent, i.e. $R_{ip}=R_i-R_{id}$).

Figure 4:
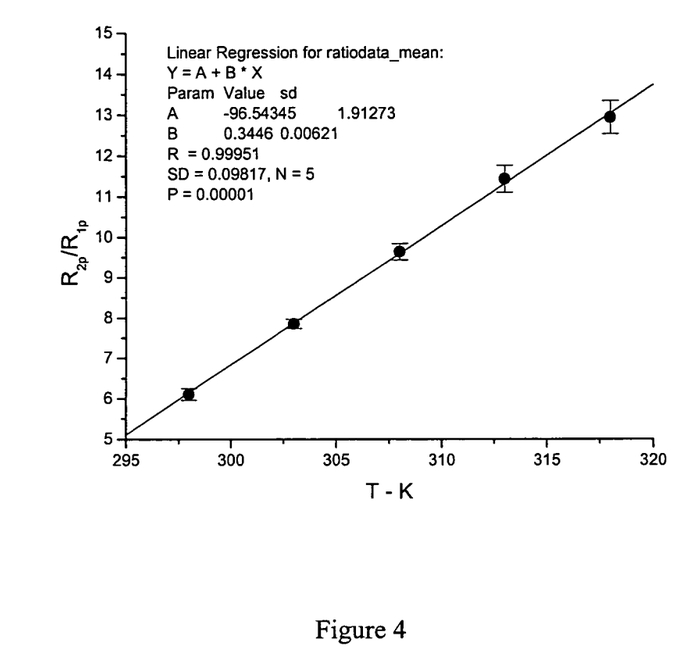

In the investigated temperature range, the $R_{2p}/R_{1p}$ ratio is linear with a positive slope of ca. 0.35 units/degree (FIG. 4).

Importantly, the deviation between the $R_{2p}/R_{1p}$ values for the three solutions at a given temperature is very small, thus demonstrating the validity of this approach. The increase of $R_{2p}/R_{1p}$ values upon increasing temperature is the result of a significant involvement of $\tau_R$ in determining the transverse relaxation rate. In fact, the $R_{2p}$ values increases with temperature, whereas $R_{1p}$ values display an opposite tendency. This means that $\tau_M$ values in the range of temperature considered are likely in the middle between $T_{2M}$ and $T_{1M}$ ($T_{1M} > \tau_M > T_{2M}$).

Conversely, in the absence of Avidin, the $R_{2p}/R_{1p}$ ratio for solutions containing 0.125, 0.25, and 0.5 mM Gd-1 concentration is ca. 1.3 and, moreover, it is completely unaffected by temperature changes.

Example 2

As a proof of principle, the responsive property of a macromolecular Gd(III) complex towards pH, an other important diagnostic in vivo marker has been investigated.

In this case, the slowly tumbling system chosen was the non covalent adduct formed by Gd-DOTP (1,4,7,10-tetraazacyclododecane-1,4,7,10-tetramethylene phosphonic acid) and poly-arginine. GdDOTP is a negatively charged macrocyclic complex able to bind, via electrostatic forces, to positively charged compounds, including cationic polyamino acids like polyarginine. (Aime S, Angew Chem Int Ed 2003, 42, 4527-4529).

The inner-coordination sphere of Gd-DOTP lacks of water molecules and, therefore, the relatively high relaxivity measured for this complex has been accounted for in terms of a large second-sphere contribution arising from the presence of several water molecules tightly bound to the phosphonate groups of the chelate and, therefore, dipolarly coupled to the Gd(III) ion.

In analogy to some other cationic polyamino acids like polylysine, the tumbling motion of polyarginine is pH dependent owing to the cross-over from a faster tumbling structure (at acidic pH) due to the repulsion of the positively charged guanidine groups to a more rigid and slower tumbling α-helix structure formed at basic pH when the guanidine residues deprotonates.

The binding affinity between Gd-DOTP and polyarginine is so strong ($K_A = 3 \cdot 10^4$ as determined by relaxometric mesurements) that it is very easy to prepare a solution in which the paramagnetic complex is fully bound to the polymer.

The $R_{2p}/R_{1p}$ protocol for the pH measurement was tested on two solutions containing different amounts of Gd-DOTP/polyarginine adduct (in 10 mM HEPES buffer). The concentration of the Gd(III) complex in the two solutions was 0.25 and 0.5 mM, respectively, and the Gd-DOTP/polyarginine molar ratio was 10/1. $R_1$ and $R_2$ values for water protons were measured at 14.1 T (corresponding to a proton Larmor frequency of 600 MHz) and 312 K.

The paramagnetic $R_{1p}$ and $R_{2p}$ contributions to the observed relaxation rates were obtained by subtracting the corresponding diamagnetic contributions ($R_{id}$) measured at each pH value in the absence of the paramagnetic agent.

Figure 5:
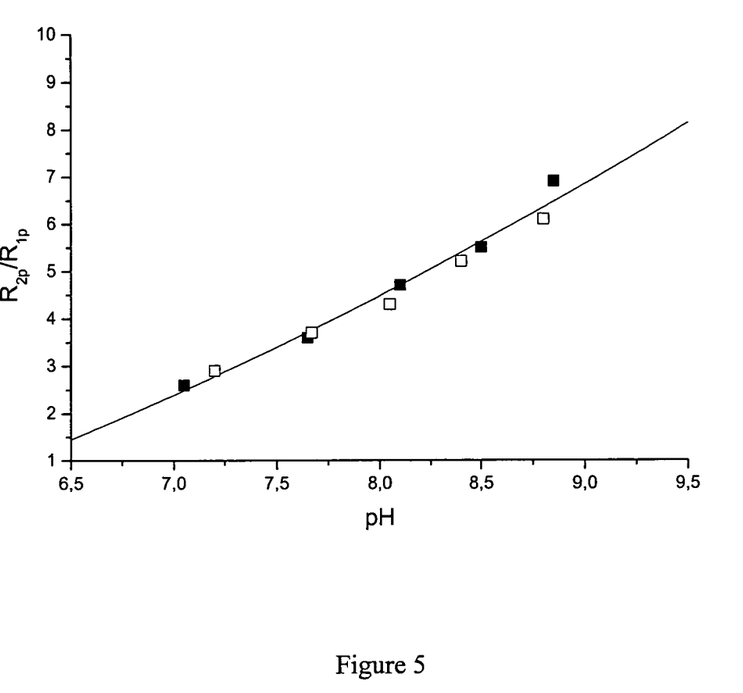
FIG. 5 reports the pH dependence of the $R_{2p}/R_{1p}$ ratio for the Gd-DOTP/polyarginine adduct (molar ratio=10) at 14.1 T and 312 K. The concentration of the Gd(III) complex was of 0.5 mM (filled squares) and 0.25 mM (open squares).

The result shown in FIG. 5 strongly support the right applicability of the proposed approach also to macromolecular systems not including any water molecule(s) coordinated to the metal centre, provided that the relaxation rates of the said systems are dominated by the contribution of dipolarly coupled water protons present in the second coordination sphere of the metal center.

Example 3

As a further proof of principle, the pH responsiveness of a macromolecular Gd(III)-based covalent adduct has been investigated.

Figure 6:
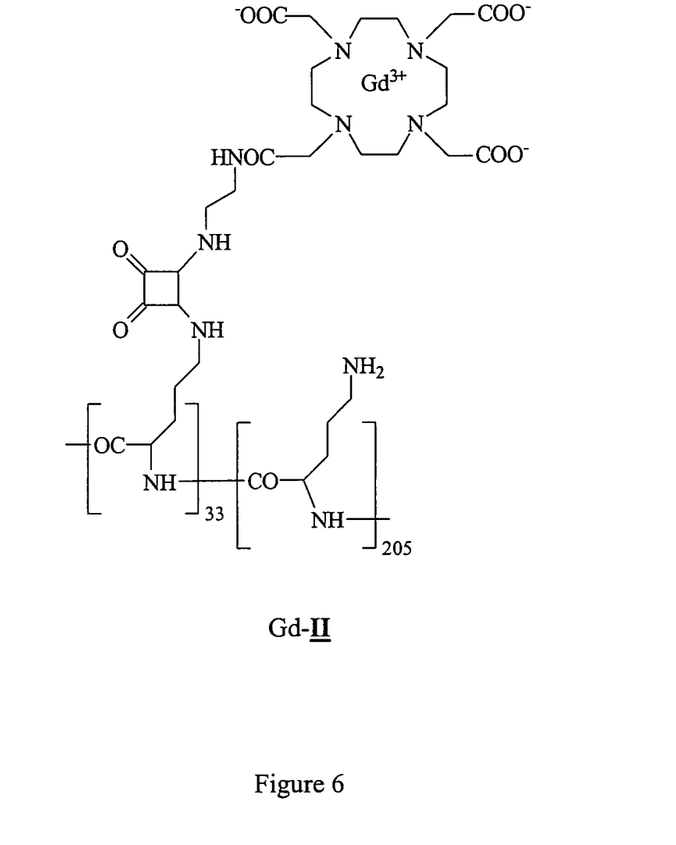
FIG. 6 shows the structure of the macromolecular adduct Gd-II.

The model system is represented by a Gd(III) chelate covalently linked, via a squaric moiety, to a poly-Ornithine backbone (Gd-II, FIG. 6).

As it has already discussed in the Example 2, it is known that basic polyamino acids, like poly-Ornithine, undergo a pH-controlled reversible conformational switch from a "random-coil" structure, predominant at pH <9 when the ornithine residues are protonated, to a "pseudo-α-helical" structure, predominant at pH >11 when the ornithine residues deprotonate (G C Hammes, P B Roberts, J Am Chem Soc, 91, 1812, 1969). Interestingly, it has been demonstrated that the rotational mobility of the two conformations are different and a longer $\tau_R$ value has been observed for the significantly more rigid and structurally ordered "pseudo-α-helical" conformation (see, for instance, S Aime, M Botta, S G Crich, G Giovenzana, G Palmisano, M Sisti, Chem Commun, 1577, 1999).

Figure 7:
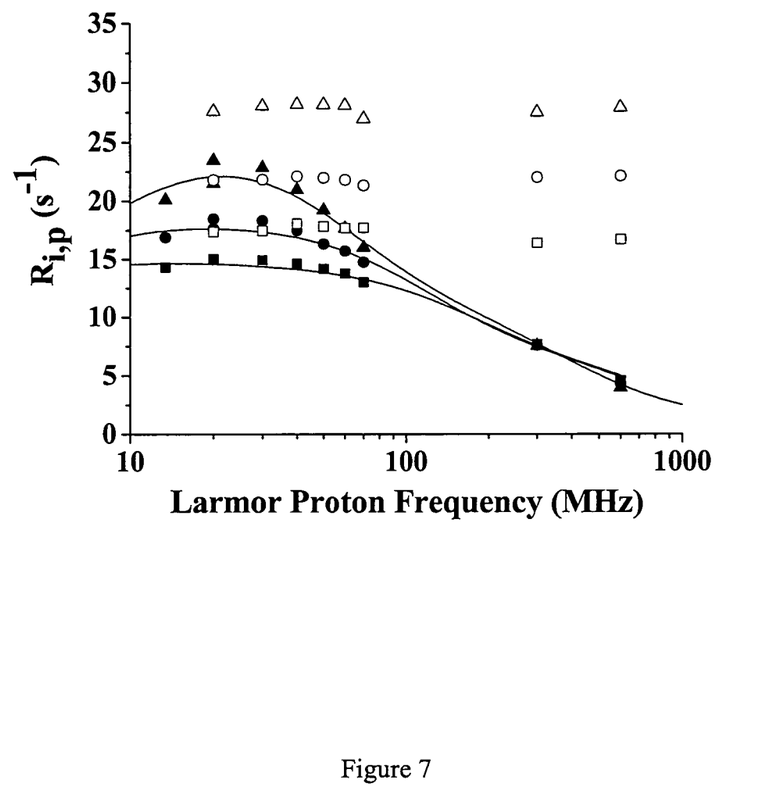
FIG. 7 reports the magnetic field dependence of $R_{1p}$ (filled symbols) and $R_{2p}$ (open symbols) measured at 25° C. and 600 MHz for a solution containing the Gd-II adduct ([Gd]=1 mM). pH 7 (squares), pH 10 (circles), and pH 12 (triangles).

FIG. 7 reports the magnetic field dependence of $R_{1p}$ and $R_{2p}$ measured at three pH values, 7, 10, and 12, of a solution of Gd-II containing 1 mM of Gd(III) ion. The $R_{1p}$ enhancement observed upon increasing pH is a clear evidence of the slowing-down of the reorientational motion of the macromolecolar complex caused by the conformational switch of the polymer. A detailed quantitative analysis of the $R_{1p}$ profiles, performed by using the Solomon-Bloembergen-Morgan theory, implemented with the Lipari-Zsabo model, indicated that both global ($\tau_R^g$) and local ($\tau_R^l$) reorientational times for the macromolecular adduct are pH-dependent ($\tau_R^g$ of 1.0, 1.7, and 3.6 ns were obtained at pH 7, 10, and 12, respectively).

Interestingly, the $R_{2p}$ values are not dependent on magnetic field, because they are dominated by $\tau_C$ and the latter parameter, in this case, is dominated by $\tau_R$. For this reason, $R_{2p}$ values are significantly affected by pH of the solution.

Figure 8:
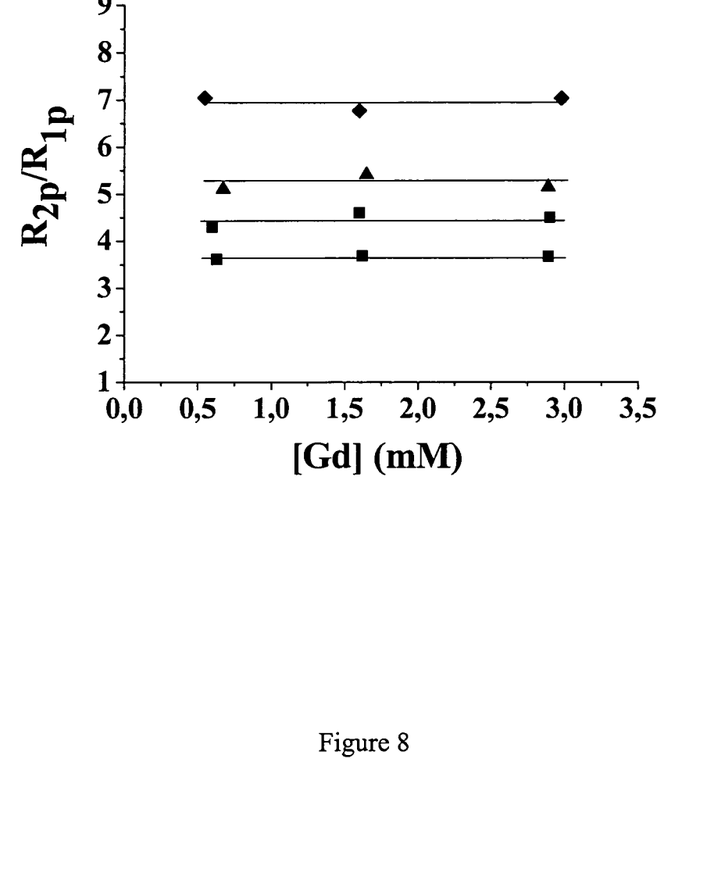
FIG. 8 reports the dependence of the $R_{2p}/R_{1p}$ ratio on the concentration of Gd(III) for the Gd-II macromolecular adduct at four pH values: pH 7 (squares), pH 8.5 (circles), pH 10 (triangles), and pH 12 (diamonds) (600 MHz. 25° C.).
Figure 9:
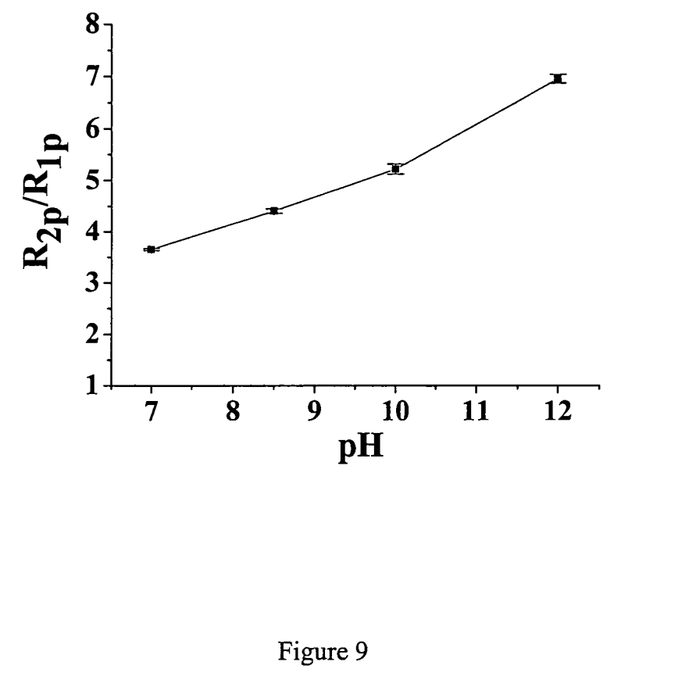
FIG. 9 shows the corresponding pH dependence of the $R_{2p}/R_{1p}$ ratio calculated from the data point reported in FIG. 8.

To confirm the concentration-independence of the $R_{2p}/R_{1p}$ ratio, the paramagnetic contributions to the relaxation rates have been measured at 14 T, 25° C., and at four pH values (7, 8.5, 10, and 12), as a function of the concentration of Gd(III) ion. The result, reported in FIGS. 8 and 9, shows unambiguously that the $R_{2p}/R_{1p}$ ratio is independent on the concentration of the macromolecular agent but dependent on the parameter of interest.

Example 4

The responsive properties towards temperature of a liposome entrapping a Gd(III) complex have been investigated as an example of a nano-sized responsive system according to the invention. The paramagnetic liposome has been prepared by hydrating a thin lipidic film made of a mixture of lipids (POPC/Chol/DSPE-PEG, molar ratio 55:40:5 wherein POPC is 1-Palmitoyl-2-Oleoyl-sn-Glycero-3-Phosphocholine, Chol is Cholesterol, and DSPE-PEG is 1,2-Distearoyl-sn-Glycero-3-Phosphoethanol-amine-N-(PolyethyleneGlycol)-2000) with a solution 200 mM of Gd-HPDO3A (a contrast agent marketed as ProHance®). Upon repeated extrusion with a filter of 400 nm of diameter, the liposome suspension has been exhaustively dialysed against isotonic Hepes buffer in order to remove the untrapped Gd(III) complex. The mean liposome diameter after dialysis was of 260 nm.

Figure 10:
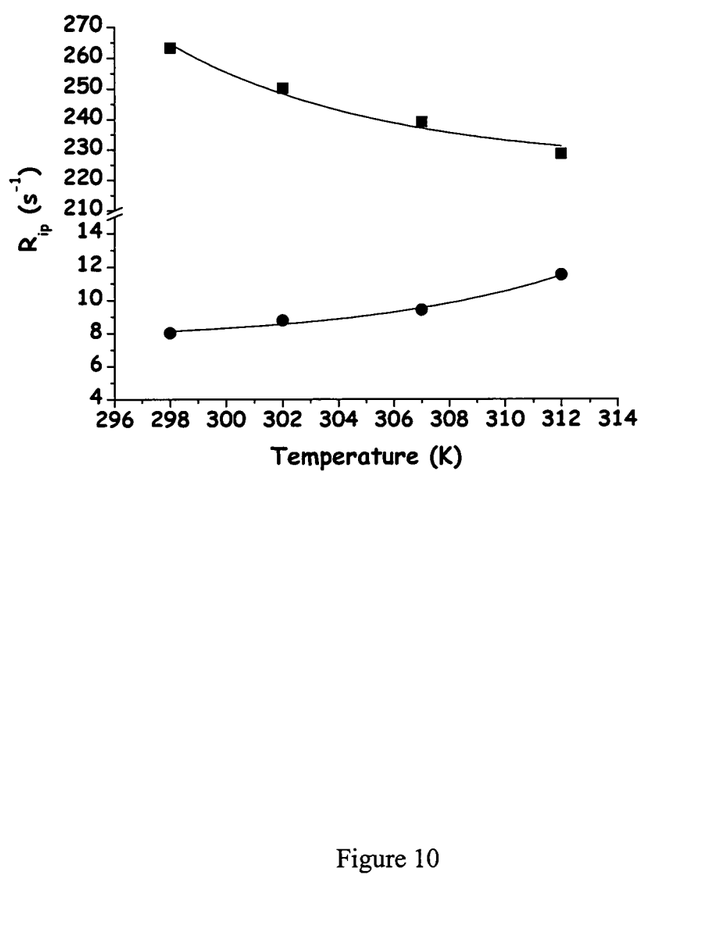
FIG. 10 reports the temperature dependence of $R_{1p}$ (circles) and $R_{2p}$ (squares) measured at 300 MHz for a solution containing paramagnetic liposomes (POPC/Chol/DSPE-PEG, molar ratio 55:40:5) entrapping GdHPDO3A 200 mM. The total concentration of the Gd(III) complex in the suspension was 6.6 mM.

FIG. 10 reports the temperature dependence of $R_{2p}$ and $R_{1p}$ for this nano-sized system, measured at 7 T. The two paramagnetic contributions show an opposite tendency upon increasing temperature: $R_{2p}$ decreases, whereas $R_{1p}$ increases.

The observed behaviour can be explained by considering that $R_{1p}$ contribution is controlled by the water permeability of the liposome membrane and, for this reason, a temperature increase lead to a Rip enhancement. On the contrary, magnetic susceptibility effects, whose extent decrease as the temperature increases, dominate $R_{2p}$ values.

Figure 11:
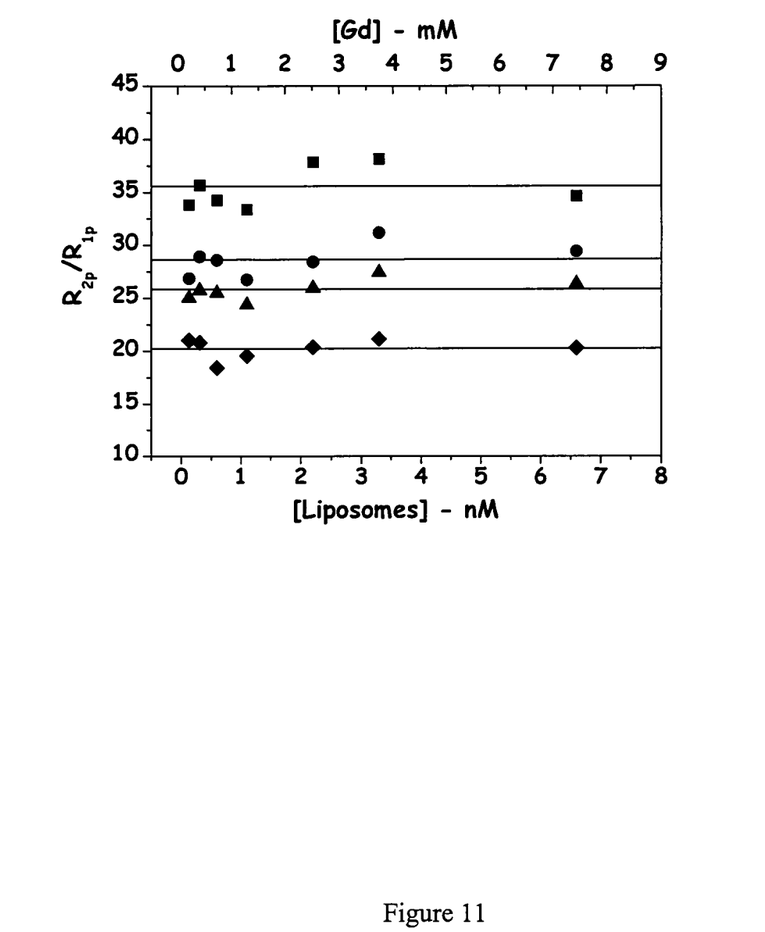
FIG. 11 shows the dependence of the $R_{2p}/R_{1p}$ ratio on the concentration of liposomes (bottom x-axis) and Gd(III) (top x-axis) for the paramagnetic liposomes described in Example 4. Temperatures: 298 K (squares), 302 K (circles), 307 K (upper triangles), and 312 K (diamonds) (300 MHz).

The concentration-independence of the $R_{2p}/R_{1p}$ ratio has been demonstrated by measuring $R_{2p}$ and $R_{1p}$ values of solutions containing different amounts of liposomes (and consequently of Gd(III) complex, FIG. 11).

Figure 12:
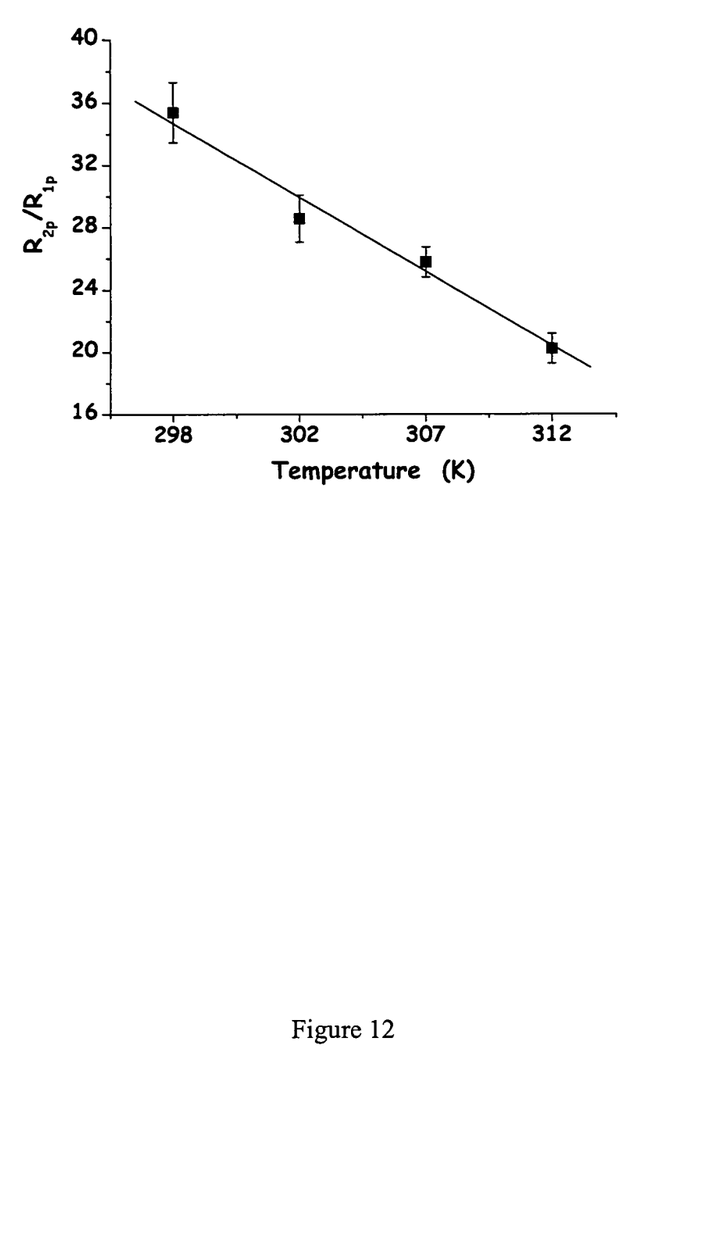
FIG. 12 shows the strong dependence of the $R_{2p}/R_{1p}$ ratio on temperature.

The different behaviour displayed by $R_{1p}$ and $R_{2p}$ versus temperature makes the $R_{2p}/R_{1p}$ ratio strongly dependent on this parameter (FIG. 12).

The invention claimed is:

1. A method for the in vivo determination, by use of the MRI technique, of the value of a physical or chemical parameter of diagnostic interest selected from the group consisting of temperature, pH, partial pressure of oxygen or carbon dioxide, specific ion or metabolite concentration and specific enzymatic activity in a human or animal body organ, fluid or tissue, said method comprising:
   administering to said human or animal a diagnostically effective amount of a slow tumbling paramagnetic agent that is a nano-sized system comprising a liposome entrapping HPDO3A complexed with a paramagnetic metal in an inner aqueous phase at a minimum concentration of 5 mM, and having a mean diameter $\geq 5$ nm;
   recording a MRI image;
   calculating the $R_{2p}/R_{1p}$ ratio, which acts as a reporter of a change in the parameter of interest; and
   determining the value of the parameter of interest through the obtained $R_{2p}/R_{1p}$ ratio.

2. The method of claim 1, wherein the metal of the paramagnetic complex is a Lanthanide or a Transition metal ion.

3. The method of claim 2 wherein the metal ion is selected from $Fe(^{2+})$, $Fe(^{3+})$, $Cu(^{2+})$, $Cr(^{3+})$, $Eu(^{3+})$, $Dy(^{3+})$, $La(^{3+})$, $Yb(^{3+})$ or $Mn(^{2+})$ and $Gd(^{3+})$.

4. The method of claim 3 wherein the metal ion is $Gd(^{3+})$.

5. A method for the in vivo determination, by use of the MRI technique, of the value of a physical or chemical parameter of diagnostic interest selected from the group consisting of temperature, pH, partial pressure of oxygen or carbon dioxide, specific ion or metabolite concentration and specific enzymatic activity in a human or animal body organ, fluid or tissue, said method comprising:
   administering to said human or animal a diagnostically effective amount of a slow tumbling paramagnetic agent that is a macromolecular paramagnetic metal complex endowed with at least one labile water molecule coordinated to the metal center, having a $\tau_R$ value from 1 to 10 ns and a $\tau_M$ value from 0.01 to 1 µs, and including a polyamino acid;
   recording a MRI image;
   calculating the $R_{2p}/R_{1p}$ ratio, which acts as a reporter of a change in the parameter of interest; and
   determining the value of the parameter of interest through the obtained $R_{2p}/R_{1p}$ ratio.

6. The method of claim 5, wherein the macromolecular paramagnetic metal complex is the Gd-DOTP/polyarginine adduct, or the Gd-II macromolecular adduct.

7. The method of claim 5, wherein the metal of the paramagnetic complex or agent is a Lanthanide or a Transition metal ion.

8. The method of claim 7, wherein the metal ion is selected from $Fe(^{2+})$, $Fe(^{3+})$, $Cu(^{2+})$, $Cr(^{3+})$, $Eu(^{3+})$, $Dy(^{3+})$, $La(^{3+})$, $Yb(^{3+})$ or $Mn(^{2+})$ and $Gd(^{3+})$.

9. The method of claim 8, wherein the metal ion is $Gd(^{3+})$.

* * * * *